(12) United States Patent
Lacoste et al.

(10) Patent No.: US 11,182,692 B2
(45) Date of Patent: Nov. 23, 2021

(54) MACHINE LEARNING FOR RANKING CANDIDATE SUBJECTS BASED ON A TRAINING SET

(71) Applicant: International Business Machines Corporation, Armonk, NY (US)

(72) Inventors: Alix M. Lacoste, New York, NY (US); William S. Spangler, San Martin, CA (US)

(73) Assignee: International Business Machines Corporation, Armonk, NY (US)

( * ) Notice: Subject to any disclaimer, the term of this patent is extended or adjusted under 35 U.S.C. 154(b) by 826 days.

(21) Appl. No.: 15/625,352

(22) Filed: Jun. 16, 2017

(65) Prior Publication Data

US 2018/0365589 A1 Dec. 20, 2018

(51) Int. Cl.
*G06N 20/00* (2019.01)
*G16H 50/70* (2018.01)

(52) U.S. Cl.
CPC ............ *G06N 20/00* (2019.01); *G16H 50/70* (2018.01)

(58) Field of Classification Search
CPC ........ G06N 20/00; G06N 5/043; G06N 3/088; G06N 5/022; G06F 16/00; G06F 16/30;
(Continued)

(56) References Cited

U.S. PATENT DOCUMENTS 7,346,491 B2 * 3/2008 Kanagasabai ......... G06F 40/211
704/9
7,890,505 B1 * 2/2011 Alspector ........... G06F 16/9535
707/731
(Continued)

FOREIGN PATENT DOCUMENTS

WO 2008/109874 A1 9/2008

OTHER PUBLICATIONS

Amini, Massih Reza, Tuong Vinh Truong, and Cyril Goutte. "A boosting algorithm for learning bipartite ranking functions with partially labeled data." Proceedings of the 31st annual international ACM SIGIR conference on Research and development in information retrieval. 2008. (Year: 2008).*
Allahyari, Mehdi et al. "Ontology-based text classification into dynamically defined topics." 2014 IEEE international conference on semantic computing. IEEE (Year: 2014).*
(Continued)

*Primary Examiner* — Luis A Sitiriche
*Assistant Examiner* — Adam C Standke
(74) *Attorney, Agent, or Firm* — John Noh; Edell, Shapiro & Finnan, LLC (57) ABSTRACT

According to an embodiment of the present invention, a system designates each document in a collection of documents as a member of a first group containing known subjects for a concept of interest or as a member of a second group containing candidate subjects for the concept of interest and determines a subset of documents for at least one subject. The system generates a classifier based on the documents in the first and second groups and applies the classifier to a set of documents for the at least one subject to determine whether each document belong to the first and/or second group. The system generates a score for the at least one subject based on a quantity of documents for that subject assigned to the first group of documents relative to a total quantity of documents for that subject and ranks that subject based on the determined score for each subject.

9 Claims, 8 Drawing Sheets

(58) Field of Classification Search
CPC .. G06F 16/24578; G06F 16/35; G06F 16/285; G06F 16/24573; G06F 16/3347; G06Q 50/18; G16H 50/70
USPC ............... 706/12, 20, 21, 25; 707/706, 723
See application file for complete search history.

(56) References Cited

U.S. PATENT DOCUMENTS

| | | | |
|---|---|---|---|
| 8,165,974 B2* | 4/2012 | Privault | G06Q 50/18 706/12 |
| 9,183,173 B2* | 11/2015 | Yih | G06N 20/00 |
| 9,229,988 B2 | 1/2016 | Vadrevu et al. | |
| 9,317,559 B1 | 4/2016 | Blair-Goldensohn et al. | |
| 2008/0195567 A1* | 8/2008 | Chen | G06N 5/022 706/46 |
| 2008/0319973 A1* | 12/2008 | Thambiratnam | G06F 16/313 |
| 2009/0024598 A1* | 1/2009 | Xie | G06F 16/3349 |
| 2015/0186787 A1* | 7/2015 | Kumar | G06F 16/93 706/12 |
| 2015/0363688 A1* | 12/2015 | Gao | G06F 16/9032 706/27 |
| 2016/0170982 A1* | 6/2016 | Djuric | G06F 16/353 707/740 |
| 2016/0306877 A1* | 10/2016 | Winther | G06F 16/334 |

OTHER PUBLICATIONS

Takano, Kosuke et al. "A framework for a feedback process to analyze and personalize a document vector space in a feature extraction model." Information Technology and Management 10.2 (Year: 2009).*

Truong et al., "Learning to Rank with Partially Labeled Training Data", http://ama.liglab.fr/~amini/Publis/Lm2RnkwithPartLblTrndata-Inscit06.pdf, retrieved from internet Apr. 2017, 5 pages.

* cited by examiner

MACHINE LEARNING FOR RANKING CANDIDATE SUBJECTS BASED ON A TRAINING SET

BACKGROUND

1. Technical Field

Present invention embodiments relate to machine learning and, more specifically, to creating a training set based on a plurality of documents related to a set of known subjects and a set of candidate subjects and employing machine learning to rank the one or more candidate subjects based on the training set.

2. Discussion of the Related Art

Classifying known entities based on their characteristics allows researchers to predict the likelihood that entities having similar characteristics to those of the known entities may be similarly classified, and therefore be expected to exhibit similar properties, attributes, etc. This is particularly useful in pathology diagnoses, where hundreds of proteins may be related to a given disease, e.g., cardiovascular disease. Current methods of classifying entities are based on creating a supervised training set of positive and negative examples. Unfortunately, this method requires a large number of labeled entities to serve as positive and negative examples and may result in a model that is not general enough, i.e., is overspecialized. Furthermore, these models can become very unstable (i.e. small changes in the features of an example may cause drastic changes in its classification), making them inappropriate for accurately classifying small candidate sets.

SUMMARY

According to an embodiment of the present invention, a system designates a first subset of known subjects belonging to a concept of interest and a second subset of candidate subjects for the concept of interest. The system further designates each document in a collection of documents as a member of a first group of documents containing known subjects in the first subset or as a member of a second group of documents containing candidate subjects in the second subset and determines a subset of documents for at least one subject in the collection of documents. The system then generates a classifier based on the designated documents in the first and second groups of documents and applies the classifier to at least the subset of documents for the at least one subject to determine whether the at least one subject document belongs to the first and/or second groups of documents. The system further generates a score for the at least one subject based on a quantity of documents for that subject assigned to the positive group of documents relative to a total quantity of documents for the at least one subject and ranks the at least one subject based on the determined score for the at least one subject. Embodiments of the present invention further include a method and computer program product for ranking candidate subjects based on a training set in substantially the same manner described above.

DETAILED DESCRIPTION

Present invention embodiments dynamically rank candidate subjects (e.g., item, entity, person, disease, etc.) based on a generated training set. Initially, a server receives and analyzes a collection of documents to categorize each of the documents in the collection as either a member of a first group of documents containing known subjects for a concept of interest, or as a member of a second group of documents containing potential candidate subjects for the concept of interest and determines, for each subject, a set of the documents that describe the known and candidate subjects. The server may then generate a dictionary of words and/or phrases that frequently occur within the text of each subject document and, based on the dictionary, may build a vector space model of the document collection, wherein each vector corresponds to a single document in the collection and the dimensions of the vector correspond to the terms identified in the dictionary. Using the vector space model and machine learning, the system may further generate a classifier (e.g., binary classifier, Bayes classifier, etc.) based on the designated documents in the first and second groups of documents and apply the classifier to the collection of documents to determine whether each of the subject documents belongs to the first or second groups of documents.

For each subject, the system may then generate a score based on a quantity of subject documents having document vectors assigned to the first group of documents relative to a total quantity of the subject documents and ranks the subjects based on the determined score for each subject. Embodiments of the present invention further include a method and computer program product for ranking candidate entities based on a training set in substantially the same manner described above.

Figure 1:
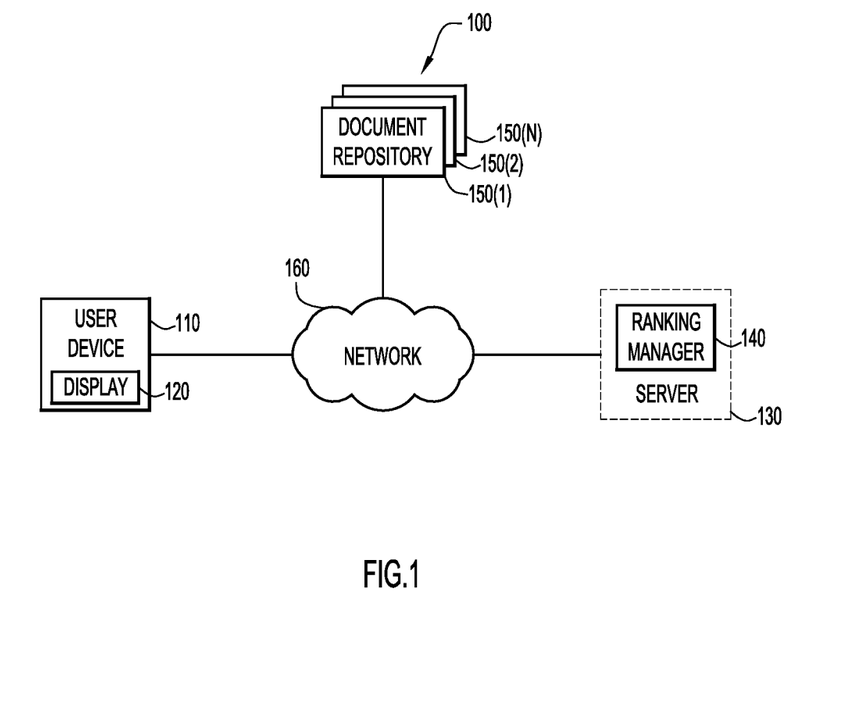
FIG. 1 is a diagrammatic illustration of an example computing environment for use with an embodiment of the present invention.

An example computing environment for use with present invention embodiments is illustrated in FIG. 1. Specifically, environment 100 includes a user device 110, one or more servers 130, and one or more document repositories 150. Server 130 may comprise one or more ranking managers 140, which are responsible for generating a training set of documents and employing machine learning to dynamically rank subjects based on the training set. Server 130 and user device 110 may be remote from each other and communicate over a network 160. Network 160 may be implemented by any number of any suitable communications media (e.g., wide area network (WAN), local area network (LAN), Internet, Intranet, etc.). Alternatively, server 130 and user device 110 may be local to each other, and communicate via any appropriate local communication medium (e.g., local area network (LAN), hardwire, wireless link, Intranet, etc.).

User device 110 enables users to receive one or more scored rankings of a plurality of subjects related to one or more concepts based on one or more training sets generated at server 130 and to display the one or more scored rankings on display 120. For example, user device 110 may receive a scored ranking of a plurality of candidate proteins that may be related to a specific disease's pathophysiology. Server 130 may rank the plurality of candidate proteins based on a training set of proteins already known to be related to the disease.

Initially, server 130 may receive a request from user device 110 to rank a plurality of subjects based on a collection of documents related to the plurality of subjects and stored in user device 110, server 130, and/or one or more document repositories 150. After receiving the request from user device 110, server 130 may receive a plurality of documents from user device 110 and/or one or more document repositories 150, and analyze the plurality of documents to categorize each document as either a member of a first group of documents containing known subjects related to a concept of interest, or as a member of a second group of documents containing potential candidate subjects related to the concept of interest. Server 130 may then determine, for each subject, a subset of the plurality of documents that describe the known subjects and/or the candidate subjects.

Server 130 may further generate a dictionary of words and/or phrases that frequently occur within the text of each document in the first and second groups and, based on the dictionary, may build a vector space model of the document collection, wherein the dimensions of the vector space model correspond to the terms identified in the dictionary. Using the vector space model, the system may generate a classifier based on the machine learning using designated documents in the first and second groups of documents and apply the classifier to the collection of documents to determine whether each of the subject documents belongs to the first or second groups of documents. For each candidate subject, server 130 may further generate a score based on a quantity of subject documents having document vectors assigned to the first group of documents relative to a total quantity of the subject documents and rank each of the candidate subjects based on the determined score.

Figure 2:
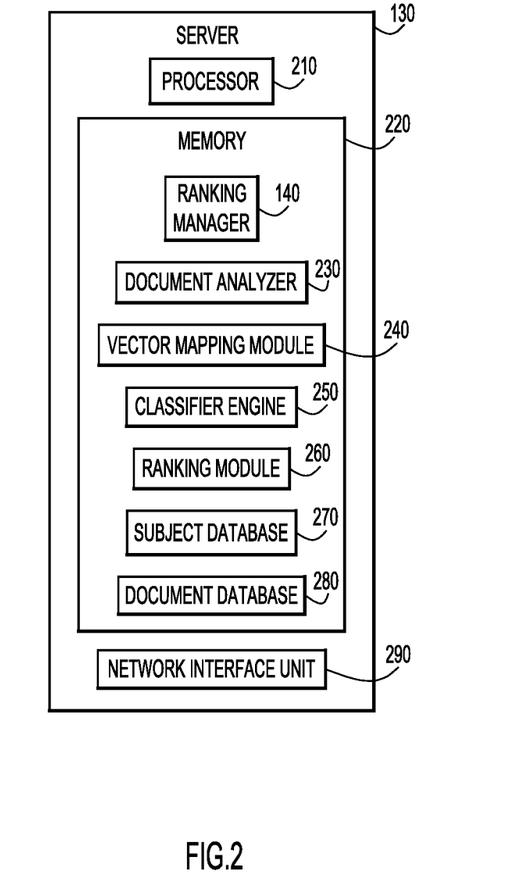
FIG. 2 is a block diagram illustrating the server of FIG. 1 in more detail according to an embodiment of the present invention.

Reference is now made to FIG. 2, which shows an example block diagram of server 130 configured for candidate subject ranking according to present invention embodiments. It should be understood that there are numerous possible configurations for server 130 and FIG. 2 is meant to be an example of one of the possible configurations. Server 130 includes a processor 210, a memory 220, and a network interface unit 290. The network interface (I/F) unit (NIU) 290 is, for example, an Ethernet card or other interface device that allows the server 130 to communicate over communication network 160. Network I/F unit 290 may include wired and/or wireless connection capabilities.

Processor 210 may include a collection of microcontrollers and/or microprocessors, for example, each configured to execute respective software instructions stored in the memory 220. Portions of memory 210 (and the instructions therein) may be integrated with processor 210.

Memory 220 may comprise read only memory (ROM), random access memory (RAM), magnetic disk storage media devices, optical storage media devices, flash memory devices, electrical, optical, or other physical/tangible (e.g., non-transitory) memory storage devices. Thus, in general, memory 220 may comprise one or more computer readable storage media (e.g., a memory device) encoded with software comprising computer executable instructions and when the software is executed (e.g., by processor 210) it is operable to perform the operations described herein. For example, memory 220 stores or is encoded with instructions or modules for ranking manager 140, which is configured to generate a classifier and, using the classifier, rank a plurality of candidate subjects and forward the ranking to user device 110 for display to a user. Optionally, user device 110 and/or server 130 may, individually or in combination, include ranking manager 140 to perform the ranking of a plurality of candidate subjects based on a score determined using a classifier.

Memory 220 may further store or is encoded with instructions for ranking manager 140 to perform overall control of the ranking operations described herein by analyzing a plurality of received documents that describe known and candidate subjects to rank a plurality of candidate subjects, including document analyzer 230, vector mapping module 240, classifier engine 250, ranking module 260, subject database 270 and document database 280. Ranking manager 140 is further configured to receive one or more requests from user device 110 to rank a plurality of candidate subjects and, in response, send one or more requests to one or more document repositories 150 for a plurality of documents associated with one or more known subjects and/or the plurality of candidate subjects. Ranking manager 140 is further configured to store the received plurality of documents in a document collection stored in document database 280 for further subject ranking operations.

Document analyzer 230 may be configured to label a set of documents by using one or more techniques (e.g., Natural Language Processing, machine learning, etc.) to analyze a plurality of documents and, based on the analysis, identify each of the plurality of documents as being positive (e.g., describing a known subject), and/or negative (e.g., describing a candidate subject). For example, if document analyzer 230 receives a document describing one or more proteins (or subjects) known to be related to a specific cardiovascular disease (or concept of interest), document analyzer 230 may identify the document as being positive. Similarly, if document analyzer receives a document describing one or more candidate proteins being ranked, document analyzer 230 may identify the document as being negative. According to an embodiment of the present invention, if document analyzer 230 receives a document describing both one or more known subjects and one or more candidate subjects, document analyzer 230 may identify the document as being both positive and negative.

For each document in a received collection of documents, vector mapping module 240 may be configured to identify, using one or more techniques (e.g., Natural Language Processing, machine learning, etc.), one or more features related to one or more subjects described in each document and to determine a document vector associated with each document. The dimensions of the document vector are related to the one or more features (e.g., heart, lipid, stroke, etc.) identified in the document. According to an embodiment of the present invention, vector mapping module 240 may be further configured to determine the dimensions of a document vector by normalizing the frequency with which each of the one or more features appears in a document associated with the document vector.

Classifier engine 250 may be configured to build a training set of documents and, based on the training set of documents and machine learning, generate a classifier that may be used to rank a plurality of candidate subjects. For example, classifier engine 250 may build a training set by selecting a plurality of documents identified by document analyzer 230 as being positive and a plurality of documents identified as being negative. According to an embodiment, the number of negative documents significantly exceeds the number of positive documents and, consequently, the classifier engine 250 may select each of the documents identified by document analyzer 230 as being positive and a random sample of documents identified by document analyzer 230 as being negative. According to a further embodiment, classifier engine may be configured to balance a training set, such that the number of negative documents included in the training set is equal to, or approximately equal to, the number of positive documents included in the training set.

Classifier engine 250 may be further configured to generate a classifier over the feature vectors associated with each of the documents included in a training set. For example, classifier engine 250 may be configured to generate a classifier vector space comprising a plurality of positive dimensions and a plurality of negative dimensions, wherein the positive dimensions of the classifier vector space correspond to document vectors associated with the documents classified as positive in the training set and the negative dimensions of the classifier vector space correspond to document vectors associated with the documents classified as negative in the training set.

Ranking module 260 may be configured to determine a ranking score for each candidate subject and, based on the ranking score, rank each of the candidate subjects (e.g., ascending order, descending order, etc.). Ranking module 260 may be further configured to determine the number of documents associated with each candidate subject identified as being positive and the number of documents identified as being negative by applying a classifier generated by classifier engine 250 to each document vector associated with a candidate subject to determine whether the document is positive and/or negative. Ranking module 260 may then determine the ranking score for the candidate subject based on the relative number of positive documents to the total number of documents associated with the candidate subject. For example, ranking module 260 may identify that 25 positive documents associated with a candidate protein contain language that is similar to documents associated with the set of training proteins and that 25 negative documents are further associated with the candidate protein. Accordingly, ranking module 260 may determine the ranking score associated with the candidate protein as: $25/(25+25)=0.5$.

Ranking manager 140, document analyzer 230, vector mapping module 240, classifier engine 250, and ranking module 260 may include one or more modules or units to perform the various functions of present invention embodiments described below. The various modules (e.g., ranking manager, document analyzer, vector mapping module, classifier engine, ranking module, etc.) may be implemented by any combination of any quantity of software and/or hardware modules or units, and may reside within memory 220 of server 130 for execution by processor 210.

Memory 220 may further provide subject database 270, which stores various information related to a plurality of known and/or candidate subjects associated with a document collection for ranking of the plurality of candidate subjects, and document database 280, which stores various information related to a plurality of documents included in one or more document collections. For example, subject database 270 may store characteristics associated with a plurality of proteins known to be related to a specific cardiovascular disease and/or characteristics associated with candidate proteins potentially related to the cardiovascular disease. Similarly, document database 280 may store a plurality of documents and/or document vectors related to the plurality of proteins known to be related to a specific cardiovascular disease and/or the candidate proteins potentially related to the cardiovascular disease. Subject database 270 and document database 280 may be implemented by any conventional or other database or storage unit, may be local to or remote from server 130, and may communicate via any appropriate communication medium (e.g., local area network (LAN), wide area network (WAN), Internet, hardwire, wireless link, Intranet, etc.).

Server 130 may be implemented by any conventional or other computer systems preferably equipped with a display or monitor, a base (e.g., including at least one processor 210, one or more memories 220 and/or internal or external network interfaces or communications devices 290 (e.g., modem, network cards, etc.), optional input devices (e.g., a keyboard, mouse or other input device), and any commercially available and custom software (e.g., server/communications software, ranking manager, etc.).

Figure 3:
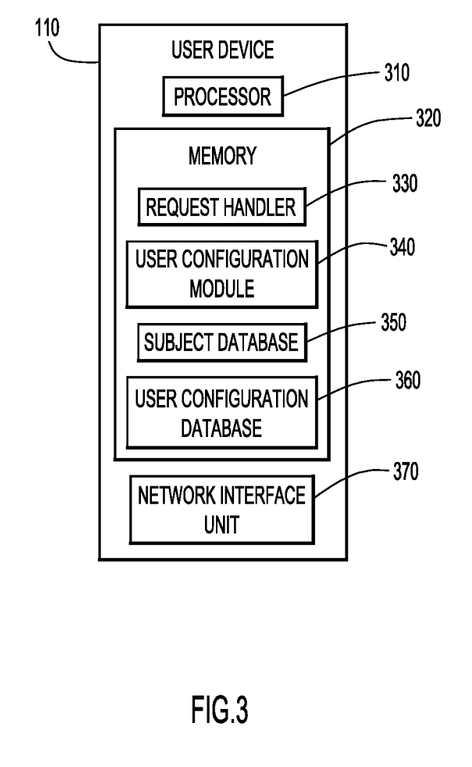
FIG. 3 is a block diagram illustrating the user device of FIG. 1 in more detail according to an embodiment of the present invention.

Reference is now made to FIG. 3, which shows an example block diagram of a user device 110 configured to request and receive a ranking of a plurality of candidate subjects according to present invention embodiments. It should be understood that there are numerous possible configurations for user device 110 and FIG. 3 is meant to be an example of one of the possible configurations. User device 110 includes a processor 310, a memory 320 and a network interface unit 370. The network interface (I/F) unit (NIU) 370 is, for example, an Ethernet card or other interface device that allows user device 110 to communicate over communication network 160. Network I/F unit 370 may include wired and/or wireless connection capabilities.

Processor 310 may include a collection of microcontrollers and/or microprocessors, for example, each configured to execute respective software instructions stored in the memory 320. Memory 320 may include various modules for execution by processor 310, including request handler 330, and user configuration module 340, subject database 350, and user configuration database 360. Portions of memory 320 (and the instructions or modules therein) may be integrated with processor 310.

Memory 320 may comprise read only memory (ROM), random access memory (RAM), magnetic disk storage media devices, optical storage media devices, flash memory devices, electrical, optical, or other physical/tangible (e.g., non-transitory) memory storage devices. Thus, in general, memory 320 may comprise one or more computer readable storage media (e.g., a memory device) encoded with software comprising computer executable instructions and when the software is executed (e.g., by processor 310) it is operable to perform the operations described herein. For example, memory 320 stores or is encoded with instructions for request handler 330 to perform overall control of the requesting, receiving and displaying operations of the ranking of a plurality of candidate subjects described herein by receiving one or more inputs from multiple components, including user configuration module 340, subject database 350, and user configuration database 360. Request handler 330 is further configured to send one or more requests to rank a plurality of candidate subjects, and information associated with the plurality of candidate subjects and a plurality of known subjects, to ranking manager 140 to determine, based on the received information associated with the known and candidate subjects, a ranking of the plurality of candidate subjects for display on user device 110.

User configuration module 340 is configured to allow a user to set one or more parameters and/or user preferences associated with the user and/or related to the display of one or more candidate subject rankings on user device 110. Accordingly, user configuration module 340 allows a user to set a user ranking and/or display preference such that incoming candidate rankings are displayed in accordance with the user's preference. It should be understood that user configuration module 340 may use any input device and/or graphical user interface (GUI) to receive one or more parameters and/or user preferences from a user associated with user device 110.

Request handler 330 and user configuration module 340 may include one or more modules or units to perform the various functions of present invention embodiments described below. The various modules (e.g., request handler, user configuration module, etc.) may be implemented by any combination of any quantity of software and/or hardware modules or units, and may reside within memory 320 of user device 110 for execution by processor 310.

Memory 320 may further provide subject database 350, which stores various information related to known and candidate subjects, and user configuration database 360, which stores various information used and generated by request handler 330 for requesting and displaying one or more rankings of a plurality of candidate subjects on user device 110. For example, subject database 350 may store various information related to a plurality of known and/or candidate subjects associated with a document collection, and user profile database 360 may store one or more characteristics or preferences associated with a user (e.g., security preferences, ranking preferences, etc.). Subject database 350 and user profile database 360 may be implemented by any conventional or other database or storage unit, may be local to or remote from server 130, and may communicate via any appropriate communication medium (e.g., local area network (LAN), wide area network (WAN), Internet, hardwire, wireless link, Intranet, etc.).

Figure 4:
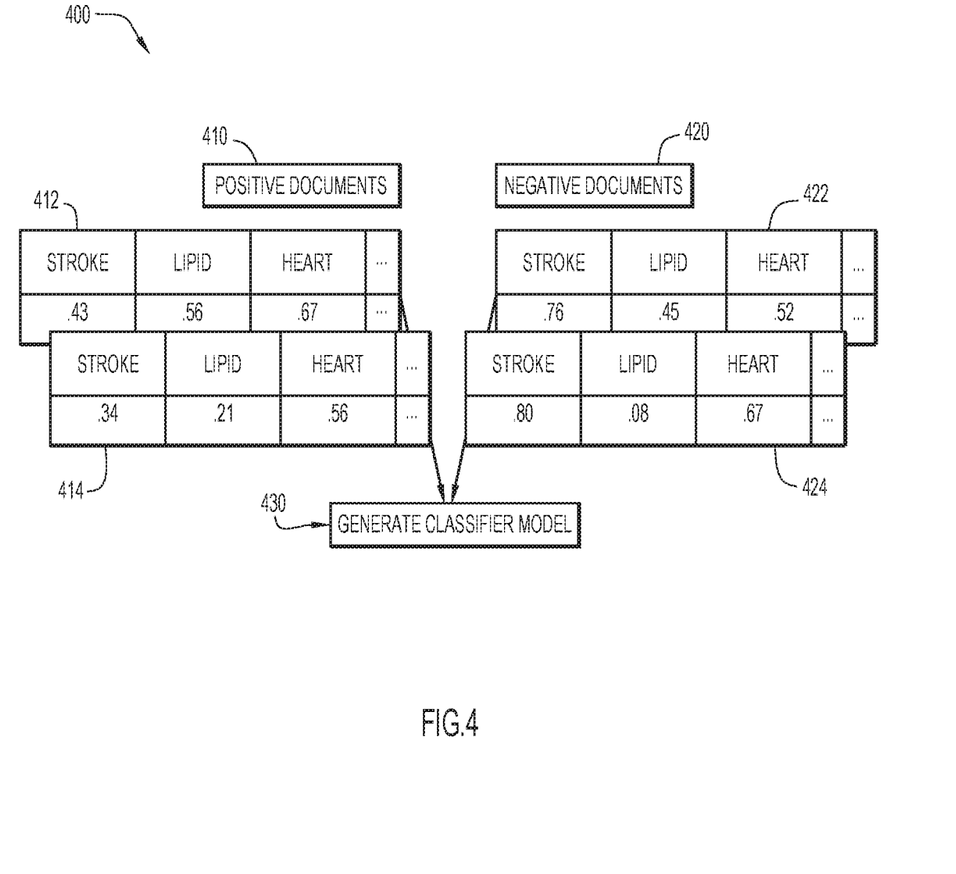
FIG. 4 is a diagrammatic illustration of a manner in which a classifier model based on a plurality of documents is created according to an embodiment of the present invention.

A diagrammatic illustration 400 of generating a classifier according to an embodiment of the present invention is illustrated in FIG. 4. Initially, server 130 may receive a request from user device 110 to rank a plurality of candidate subjects, e.g., proteins potentially related to one or more cardiovascular diseases (e.g., stroke). In response to receiving the request from user device 110, server 130 may receive and collect a plurality of positive documents 410 and a random or other sample of negative documents 420 from user device 110 and/or one or more document repositories 150. The plurality of positive documents 410 are associated with one or more proteins known to be related to the one or more cardiovascular diseases and the negative documents 420 are associated with the plurality of candidate subjects potentially related to the one or more cardiovascular diseases.

After receiving the plurality of positive documents 410 and negative documents 420, server 130 may generate document vectors 412 and 414 associated with positive documents 410 and document vectors 422 and 424 associated with negative documents 420. For example, vector mapping module 240 may be configured to identify, using one or more techniques (e.g., Natural Language Processing, machine learning, etc.), one or more features (e.g., stroke, lipid, heart, etc.) included in positive documents 410 and/or negative documents 420 related to the one or more cardiovascular diseases and to map each document in document collection 410 and/or document collection 420 to document vectors, e.g. 412, 414, 422, 424, having dimensions corresponding to the one or more features.

After identifying the one or more features related to the one or more cardiovascular diseases, vector mapping module 240 may determine a positive document vector associated with each document in positive documents 410, e.g., vectors 412 and 414, wherein the dimensions of positive document vectors 412 and 414 are related to the one or more features identified in a first positive document and a second positive document, respectively. According to an embodiment of the present invention, vector mapping module 240 may determine the dimensions of a document vector associated with a document by normalizing the frequency with which each of the one or more features appears in the document. For example, as shown in FIG. 4, vector mapping module 240 may determine positive document vector 412 as indicating that the normalized frequencies of the identified features (e.g., stroke, lipid, and heart) occurring within a first positive document are 0.43, 0.56, and 0.67. Accordingly, positive document vector 412 indicates that the normalized frequency of the feature "heart" occurring within the first positive document is approximately 1.5 times that of the feature "stroke." Similarly, vector mapping module 240 may determine positive document vector 414 as indicating the normalized frequencies of the identified features occurring within a second positive document as 0.34, 0.21, and 0.56, respectively.

Vector mapping module 240 may further determine document vectors, e.g., 422 and 424, associated with a random sampling of the documents included in negative documents 420, wherein the dimensions of negative document vectors 422 and 424 are related to the one or more features occurring in the document. For example, as further shown in FIG. 4, vector mapping module 240 may determine negative document vector 422 as indicating the normalized frequencies that the identified features (e.g., stroke, lipid, and heart) occur within a first negative document are 0.76, 0.45, and 0.52, respectively. Similarly, vector mapping module 240 may determine negative document vector 424 as indicating that the relative frequencies of the features occurring within a second negative document as 0.80, 0.08, and 0.67, respectively. Accordingly, negative document vector 424 indicates that the relative normalized frequency of the feature "stroke" is ten times greater than that of the feature "lipid" in the second negative document. According to an embodiment of the present invention, to balance the classifier model, the number of documents randomly sampled from negative documents 420 may be equal to, or approximately equal to, the number of documents selected from positive documents 410.

After generating positive document vectors 412 and 414 and negative document vectors 422 and 424, server 130 may generate a classifier model 430 based on the positive document vectors, e.g., 412 and 414, and the negative document vectors, e.g., 422 and 424. For example, classifier engine 250 may generate a classifier vector space associated with binary model 430 based on document vectors 412, 414, 422 and 424 that may be used to classify each of the plurality of candidate subjects.

Figure 5:
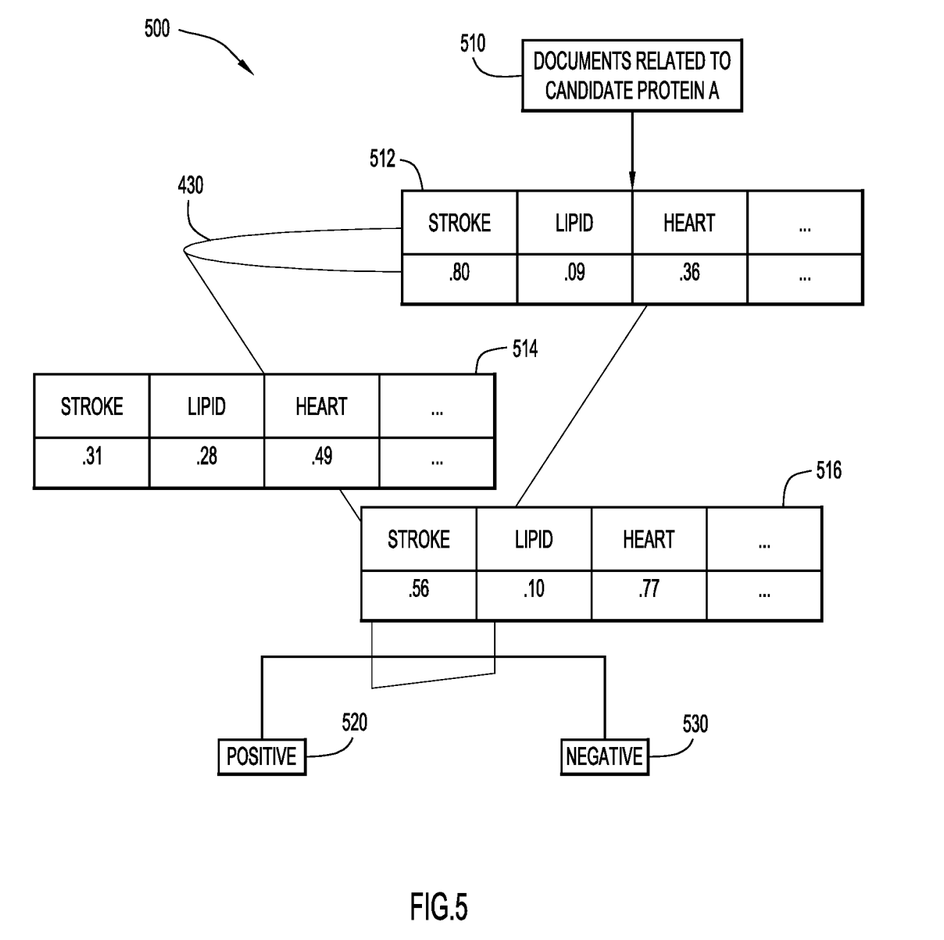
FIG. 5 is a diagrammatic illustration of a manner in which a plurality of documents related to one or more entities are classified using the classifier model of FIG. 4 according to an embodiment of the present invention.

A diagrammatic illustration 500 of classifying individual documents associated with a candidate subject using the binary model of FIG. 4 according to an embodiment of the present invention is illustrated in FIG. 5.

Initially, server 130 may identify and store a plurality of documents related to a candidate subject in document collection 510, and may further generate a document vector, e.g., 512, 514, 516, associated with each of the plurality of documents in document collection 510. For example, using the features identified in FIG. 4 (e.g., stroke, lipid, heart, etc.), server 130 may identify document collection 510 related to a candidate protein A as potentially associated with a cardiovascular disease, and, using the document collection 510, vector mapping module 240 may generate document vectors 512, 514, 516 as associated with each of the documents in document collection 510.

After generating the documents vectors, e.g., 512, 514, 516, server 130 may apply the binary model of FIG. 4, e.g., 430, to classify each of the documents in document collection 510 as being either positive or negative. For example, classifier engine 250 may apply the binary model 430 to classify each of the documents associated with document vectors 512, 514, and 516 as being positive, i.e., similar to the document vectors associated with a known subject, and/or negative, i.e., similar to the document vectors associated with a candidate subject. According to an embodiment of the present invention, classifier engine 250 may use any conventional or other technique and/or method to classify each of the documents in document collection 510 based on the document vectors and model (e.g., nearest neighbor, minimum Euclidean distance, maximum-likelihood estimators, etc.).

After classifying each of the documents in document collection 510, server 130 may determine the number of positive documents 520 and negative documents 530 related to the candidate subject, e.g., candidate protein A.

Figure 6:
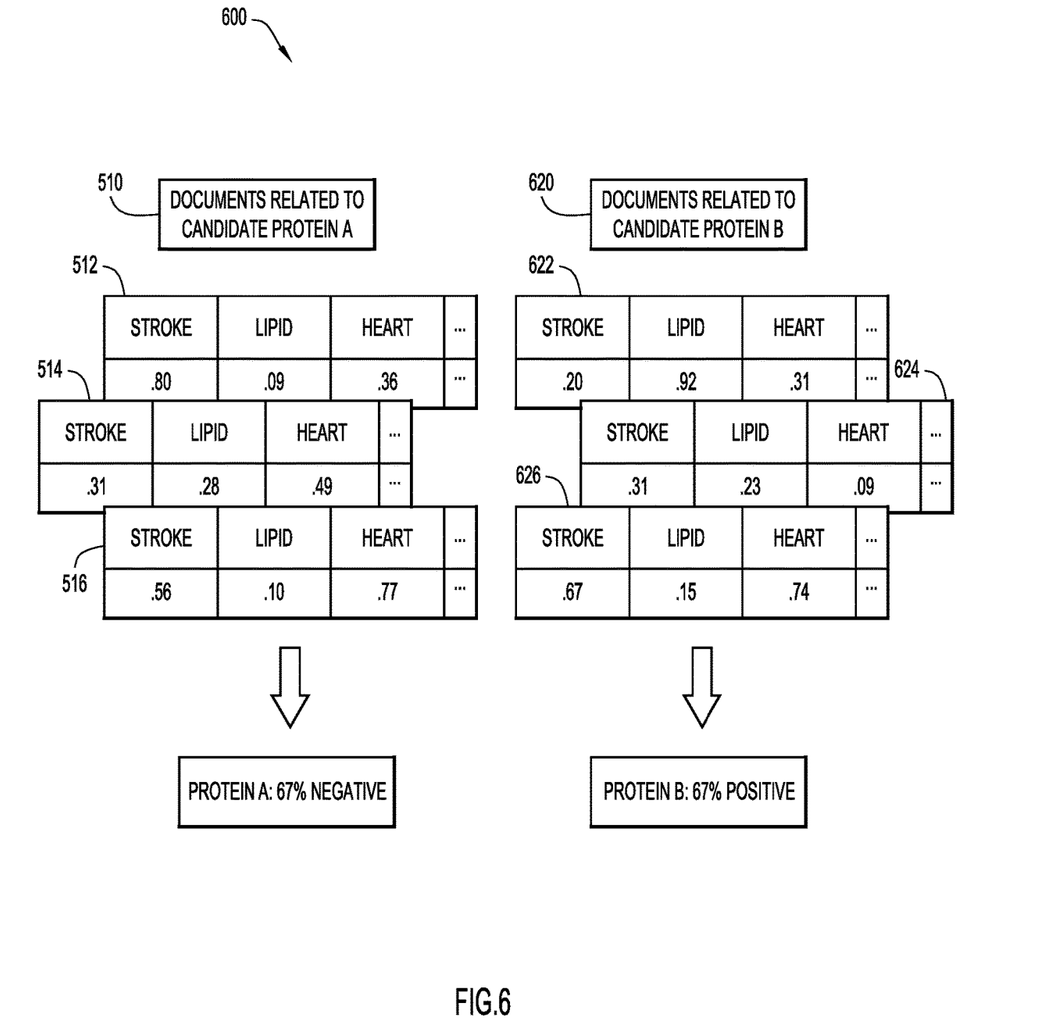
FIG. 6 is a diagrammatic illustration of a manner in which one or more entities are classified based on the classification of the plurality documents of FIG. 5 that are related to the one or more entities according to an embodiment of the present invention.

A diagrammatic illustration 600 of ranking a plurality of candidate subjects based on a classification of a plurality of documents related to each of the candidate subjects according to an embodiment of the present invention is illustrated in FIG. 6.

Initially, as discussed above in reference to FIG. 5, server 130 may generate a document vector, e.g., 512, 514, 516, for each of the plurality of documents in document collection 510 related to a candidate subject, e.g., candidate protein A. Using the document vectors and classifier engine 250, server 130 may further label each document associated with the candidate subject as being either positive (i.e., characteristic of a known subject) or negative (i.e., characteristic of a candidate subject).

Server 130 may then determine a ranking score associated with a candidate subject, e.g., candidate protein A, based on a ratio of the number of documents related to the candidate subject that are labeled as being positive to the total number of documents in a document collection, e.g., 510, related to the candidate subject. According to an embodiment of the present invention, server 130 may determine a ranking score (R) associated with a candidate subject as:

$$R=P/(P+N),\quad\text{[Equation 1]}$$

where: P=number of positive documents related to a candidate subject, and
N=number of negative documents related to a candidate subject.

For example, ranking module 260 may evaluate document vectors 512, 514 and 516 to determine that two of the documents in document collection 510 are labeled as being negative and one is labeled as being positive. That is, by evaluating the labels associated with each of the documents in document collection 510, ranking module 260 may determine that 67% of the documents related to candidate protein A are negative, i.e., are not associated with a protein known to be related to a specific cardiovascular disease. Accordingly, ranking module 260 may determine a ranking score associated with candidate protein A as: $R_A = P_A/(P_A+N_A) = \frac{1}{3} = 0.33$.

Similarly, ranking module 260 may evaluate document vectors 622, 624 and 626 to determine that two of the documents in document collection 620 are positive and one is negative. That is, by evaluating the labels associated with each of the documents in document collection 620 that are related to candidate protein B, ranking module 260 may determine that 67% of the documents related to candidate protein B are positive, i.e., describe features associated with a protein known to be related to a specific cardiovascular disease. Accordingly, ranking module 260 may determine a ranking score associated with candidate protein B as: $R_B = P_B/(P_B+N_B) = \frac{2}{3} = 0.67$.

Figure 7A:
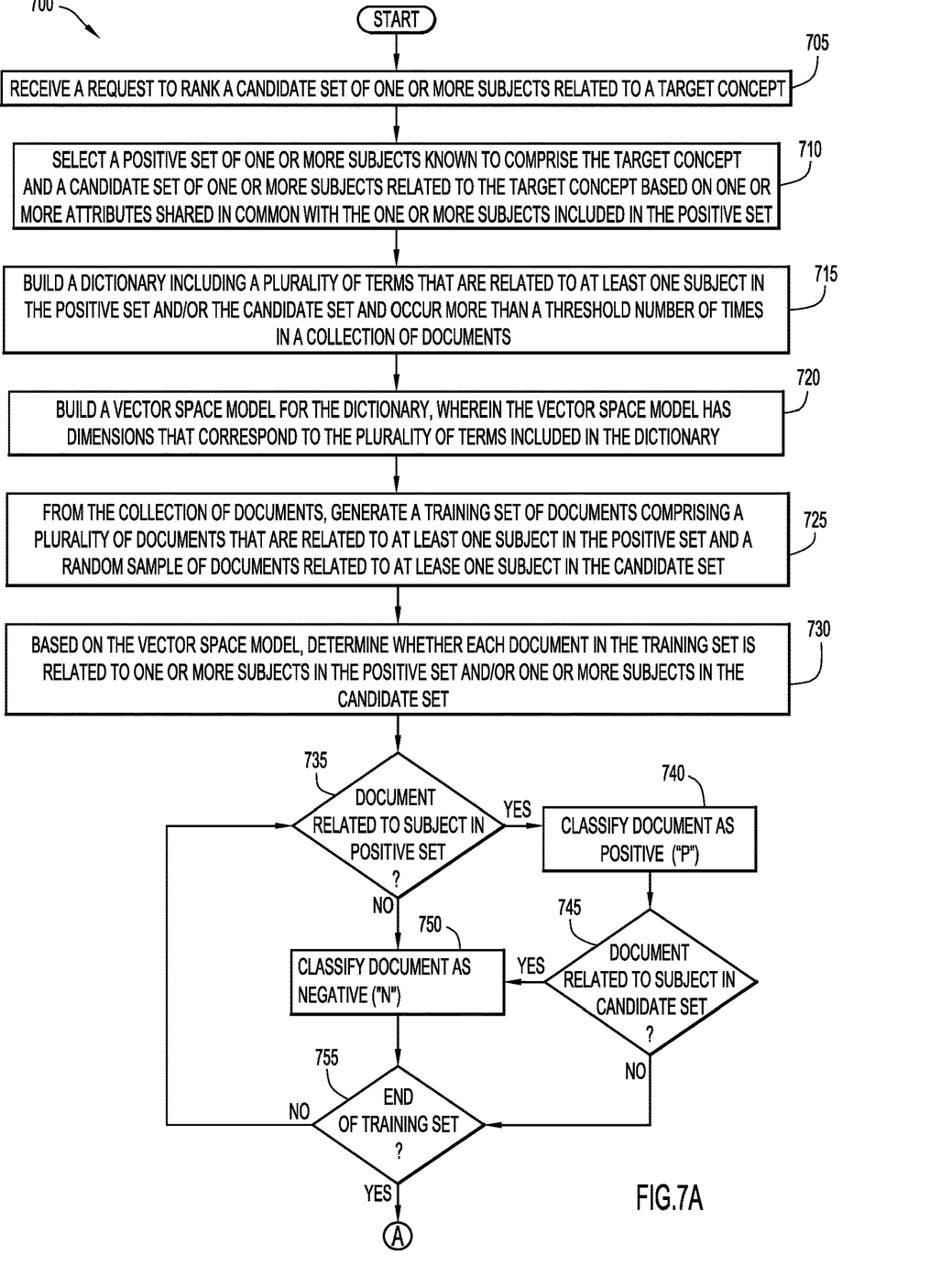
FIGS. 7A-B are a procedural flow chart illustrating a manner in which a plurality of entities in a candidate set are ranked according to an embodiment of the present invention.
Figure 7B:
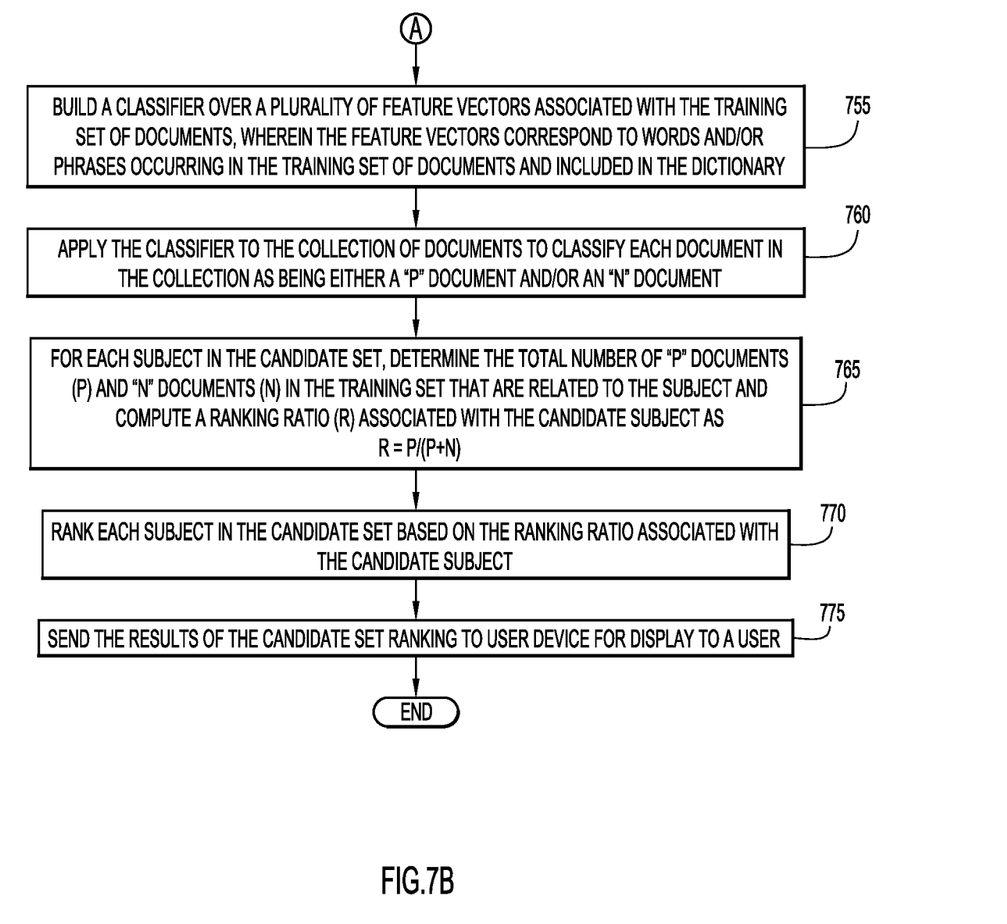

With reference to FIGS. 7A-B, there are depicted procedural flow charts illustrating a method 700 in which a training set of documents is generated and used to rank a plurality of candidate subjects. Method 700 is performed primarily by ranking manager 140.

Initially, server 130 may receive a request from user device 110 to rank a candidate set subjects related to a target concept at step 705.

A positive set of one or more subjects known to comprise the target concept is selected and a candidate set of subjects related to the target concept based on one or more attributes shared in common with the one or more subjects included in the positive set is further selected at step 710.

A dictionary of a plurality terms that are related to at least one subject in the positive set and/or the candidate set and that occur more than a threshold number of times in a collection of documents is built at step 715. For example, document analyzer 230 may determine one or more features related to a known subject and/or a candidate subject that occur more than a pre-defined threshold number of times in the training set of documents and generate a dictionary comprising the one or more features. Accordingly, the threshold number of times may be defined such that the dictionary will comprise a plurality of the most frequently occurring terms and/or features (i.e., those occurring more than the pre-configured threshold) in the collection of documents (i.e., the training set and/or candidate set). For example, the threshold may be defined such that the dictionary comprises the 20,000 (approximately) most frequently occurring terms in the training set and/or candidate set. According to a further embodiment, the threshold number may be preconfigured by a user associated with user device 110 and included in the request to rank the one or more candidate subjects.

Build a vector space model for the dictionary, wherein the vector space model has dimensions that correspond to the plurality of terms included in the dictionary at step 720. According to an embodiment of the invention, the dimensions may be normalized using any weighting or text mining scheme (e.g., Term Frequency, Inverse Document Frequency, Term Frequency-Inverse Document Frequency (TF-IDF), etc.).

From the collection of documents, a training set of documents comprising a plurality of documents that are related to at least one subject in the positive set and a random sample of documents related to at least one subject in the candidate set is generated at step 725.

Based on the vector space model, a determination is made as to whether each document in the training set of documents is related to one or more subjects in the positive set and/or one or more subjects in the candidate set at step 730.

If it is determined that a document in the training set is related to a subject in the positive set at step 735, the document is classified as being positive ("P") at step 740, otherwise, the document is classified as being negative ("N") at step 750.

After determining that the document is related to a subject in the positive set, if it is further determined that the document in the training set is also related to a subject in the candidate set at step 745, the document is also classified as being negative ("N") at step 750. Accordingly, a document therefore may be classified as being both positive and negative.

If it is determined that the end of the training set of documents has not been reached at step 755, a determination is made as to whether the next document in the training set is related to a subject in the positive set at step 735.

If it is determined that the end of the training set of documents has been reached, a classifier is built over a plurality of feature vectors associated with the training set of documents at step 755, wherein the feature vectors correspond to words and/or phrases occurring in the training set of documents and included in the dictionary.

Apply the classifier to the collection of documents to classify each document in the collection as being either a positive ("P") document and/or a negative ("N") document at step 760.

For each subject in the candidate set, a total number documents that are labeled as being "positive" (P) and a total number of documents that are labeled as being "negative" (N) are determined and, based on this determination, a ranking ratio (R) associated with the candidate subject is determined (e.g., R=P/(P+N)) at step 765.

Each subject in the candidate set is ranked based on the ranking ratio associated with the candidate subject at step 770. According to an embodiment of the present invention, any method and/or technique may be used to rank the one or more candidate subjects in the candidate set (e.g., ascending order, etc.).

The results of the candidate set ranking operations of step 770 are sent to user device 110 for display to a user at step 775, and process 700 ends.

Advantages of the present invention embodiments include ranking a plurality of candidate subjects with respect to one or more target concepts based on a dynamically generated training set built from a relatively small set of positive examples known to comprise the one or more target concepts. The system may further optimize a determination of whether one or more candidate subjects are related to one or more target concepts and, based on the determination, automatically make one or more diagnoses and/or recommendations. Furthermore, because the system may efficiently generate a training set using only a small number of positive examples, the system significantly reduces the processing time needed to generate the training set and to rank one or more candidate subjects based on the training set without compromising the accuracy of either the training set or the ranking operations.

It should be understood that embodiments of the present invention may be applied to various scenarios.

For example, the disclosed system may recommend a new automobile to a buyer based on product review articles (e.g., documents) related to new automobiles and the buyer's known preferences for past car models. In this scenario, the buyer could provide the system with a list of models of older cars that she likes (e.g., positive set); a list of a list of new car models on the market (e.g., candidate set); and a set of product review articles related to each old and new car model.

In response, the system may label each product review article as being positive if it describes a car the buyer likes and negative if it describes a candidate car. The system may then build a classifier on the labeled documents to learn the buyer's preferences. The system may further apply the classifier to the product review articles about the candidate cars. For example, the classifier may label as positive those articles written about a new car model that are similar in content to articles written about car models matching the buyer's preferences, while labeling all other documents as being negative. The system may then determine a ranking score for each candidate car based on the ratio of positive documents (P) to negative documents (N), and rank the candidate cars in ascending order based on the P/N ratio. In so doing, the system may provide the buyer with confidence that she is making an informed decision based on all available literature, without having to actually read all those articles.

As another example, the disclosed system may match people based on previous successful matches (e.g., online dating, prioritizing new job candidates, etc.) with which they were associated. In this scenario, the system may rank new candidates based on a set of known individuals with desirable characteristics (e.g., a training set). The system may analyze and classify a set writing samples (e.g., documents) from each person being ranked. For example, in online dating, the writing samples may be taken from an individual's online profile, or in prioritizing new job candidates, the writing samples may be taken from sections of the individual's resume, cover letter, and/or employer-provided questionnaires. Ranking people based on previous successful matches (e.g., online dating, prioritizing new job candidates, etc.) may therefore be successfully resolved using the disclosed classification method, despite the positive examples having a high likelihood of being scarce and heterogeneous.

In yet another example, the disclosed system may aid in medical diagnoses for neurological diseases associated with cognitive deficits, wherein such conditions can affect a patient's choice and pattern of words. In this scenario, the system may rank the possible diseases with which a given patient may be afflicted based on the patient's writing samples. The training set may include writing samples from each patient known to be afflicted by a range of neurological diseases. Accordingly, the system may classify each patient's collection of writing samples multiple times.

The system may therefore include two types of concepts in the classifier model: (i) a "patient," who is represented by the set of his/her writing samples; and (ii) a "disease," a property of each "patient." For every "disease," the positive examples may be the text samples from the afflicted patients, while the negative examples may be text samples from patients afflicted with other diseases. After generating the training set, the system may label each text sample from each patient as being either positive or negative with respect to each disease category, based on the classifier model. The system may then determine a ranking score associated with each disease for each patient based on the percentage of writing samples classified as positive with respect to the particular disease. The system may then rank each disease based on its ranking score, thereby indicating the condition, or conditions, with which a specific patient is most likely to be afflicted.

In still yet another example, the disclosed system may sub-classify a plurality of diseases to find more personalized and specific treatments for one or more patients. For example, schizophrenia is thought to be associated with a spectrum of related conditions, each having different underlying biological causes and variations in symptoms. In this scenario, a more granular stratification of patients would require training a model with few known examples due to the scarcity of positive examples. The disclosed classification method described herein, however, could successfully be used to identify one or more specific treatments for an individual schizophrenic patient, despite the relatively few positive examples.

It will be appreciated that the embodiments described above and illustrated in the drawings represent only a few of the many ways of ranking one or more candidate subjects.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.).

The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., ranking manager, document analyzer, vector mapping module, classifier engine, ranking module, etc.). These systems may include any types of monitors and input devices (e.g., keyboard, mouse, voice recognition, etc.) to enter and/or view information.

It is to be understood that the software (e.g., ranking manager, document analyzer, vector mapping module, classifier engine, ranking module, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., ranking manager, document analyzer, vector mapping module, classifier engine, ranking module, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store system information (e.g., known subject documents, candidate subject documents, user configurations, etc.). The database system may be implemented by any number of any conventional or other databases, data stores or storage structures (e.g., files, databases, data structures, data or other repositories, etc.) to store information (e.g., known subject documents, candidate subject documents, user configurations, etc.). The database system may be included within or coupled to the server and/or client systems. The database systems and/or storage structures may be remote from or local to the computer or other processing systems, and may store any desired data (e.g., known subject documents, candidate subject documents, user configurations, etc.).

The present invention embodiments may employ any number of any type of user interface (e.g., Graphical User Interface (GUI), command-line, prompt, etc.) for obtaining or providing information (e.g., known subject documents, candidate subject documents, user configurations, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion. The report may include any information arranged in any fashion, and may be configurable based on rules or other criteria to provide desired information to a user (e.g., ranking of candidate subjects, known subject information, candidate subject information, etc.).

The present invention embodiments are not limited to the specific tasks or algorithms described above, but may be utilized for any type of candidate subjects (e.g., personal, medical, business, legal, financial, etc.) to perform any type of ranking operations based on any type of known subjects (e.g., personal, medical, business, legal, financial, etc.).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method of ranking subjects for relevance to a concept of interest comprising:
   receiving, via a processor, a request including a list of a plurality of candidate subjects for determining a relationship of the candidate subjects to the concept of interest;
   designating, via the processor, a set of subjects as known subjects related to the concept of interest, wherein the candidate subjects share one or more attributes with the known subjects;
   dynamically generating for the request, via the processor, a training set comprising a portion of documents from a collection of documents, wherein the training set includes one or more documents related to at least one of the candidate subjects and one or more documents related to at least one of the known subjects;
   generating, via the processor, a dictionary of a plurality terms each related to the known subjects or the candidate subjects and occur more than a threshold number of times in the collection of documents;
   building, via the processor, a vector space model for the dictionary, wherein the vector space model has dimensions that correspond to frequencies of the plurality of terms included in the dictionary;
   designating, via the processor, each document of the training set as a member of a first group of documents containing one or more of the known subjects or a member of a second group of documents containing one or more of the candidate subjects based on the vector space model;
   determining, via the processor, feature vectors of the documents in the collection of documents, wherein the feature vectors include dimensions corresponding to frequencies of terms from the dictionary within the documents;
   generating, via the processor, a classifier for the request from the dynamically generated training set using machine learning on the feature vectors of the designated documents of the training set in the first and second groups of documents;
   applying the classifier to the feature vectors of the collection of documents, via the processor, to determine, for each candidate subject of the request, a quantity of documents for the candidate subject within the collection of documents classified as belonging to the first group of documents and a quantity of documents for the candidate subject within the collection of documents classified as belonging to the second group of documents;
   generating, via the processor, a score for each candidate subject as a ratio of the quantity of documents for the candidate subject classified as belonging to the first group of documents to a total quantity of documents in the collection of documents for that candidate subject, wherein the score indicates a relationship of the candidate subject to the concept of interest and the total quantity of documents is a sum of the quantity of documents for the candidate subject within the collection of documents classified as belonging to the first group of documents and the quantity of documents for the candidate subject within the collection of documents classified as belonging to the second group of documents;
   determining, via the processor, one or more of the candidate subjects of the request having a relationship to the concept of interest by ranking each of the candidate subjects of the request based on the determined score for each of the candidate subjects; and
   providing, via the processor, the ranked candidate subjects for display as a result of the request.

2. The method of claim 1, wherein the classifier is applied to each document in the collection of documents.

3. The method of claim 1, wherein at least one document of the training set is designated as a member of each of the first and second groups.

4. A system for ranking subjects for relevance to a concept of interest comprising:
   at least one processor configured to:
      receive a request including a list of a plurality of candidate subjects for determining a relationship of the candidate subjects to the concept of interest;
      designate a set of subjects as known subjects related to the concept of interest, wherein the candidate subjects share one or more attributes with the known subjects;
      dynamically generate for the request a training set comprising a portion of documents from a collection of documents, wherein the training set includes one or more documents related to at least one of the candidate subjects and one or more documents related to at least one of the known subjects;
      generate a dictionary of a plurality terms each related to the known subjects or the candidate subjects and occur more than a threshold number of times in the collection of documents;
      build a vector space model for the dictionary, wherein the vector space model has dimensions that correspond to frequencies of the plurality of terms included in the dictionary;
      designate each document of the training set as a member of a first group of documents containing one or more of the known subjects or a member of a second group of documents containing one or more of the candidate subjects based on the vector space model;

determine feature vectors of the documents in the collection of documents, wherein the feature vectors include dimensions corresponding to frequencies of terms from the dictionary within the documents;

generate a classifier for the request from the dynamically generated training set using machine learning on the feature vectors of the designated documents of the training set in the first and second groups of documents;

apply the classifier to the feature vectors of the collection of documents to determine, for each candidate subject of the request, a quantity of documents for the candidate subject within the collection of documents classified as belonging to the first group of documents and a quantity of documents for the candidate subject within the collection of documents classified as belonging to the second group of documents;

generate a score for each candidate subject as a ratio of the quantity of documents for the candidate subject classified as belonging to the first group of documents to a total quantity of documents in the collection of documents for that candidate subject, wherein the score indicates a relationship of the candidate subject to the concept of interest and the total quantity of documents is a sum of the quantity of documents for the candidate subject within the collection of documents classified as belonging to the first group of documents and the quantity of documents for the candidate subject within the collection of documents classified as belonging to the second group of documents;

determine one or more of the candidate subjects of the request having a relationship to the concept of interest by ranking each of the candidate subjects of the request based on the determined score for each of the candidate subjects; and provide the ranked candidate subjects for display as a result of the request.

5. The system of claim 4, wherein the classifier is applied to each document in the collection of documents.

6. The system of claim 4, wherein at least one document of the training set is designated as a member of each of the first and second groups.

7. A computer program product for ranking subjects for relevance to a concept of interest comprising:

one or more computer readable storage media collectively having program instructions embodied therewith, the program instructions executable by at least one processor to cause the at least one processor to:

receive a request including a list of a plurality of candidate subjects for determining a relationship of the candidate subjects to the concept of interest;

designate a set of subjects as known subjects related to the concept of interest, wherein the candidate subjects share one or more attributes with the known subjects;

dynamically generate for the request a training set comprising a portion of documents from a collection of documents, wherein the training set includes one or more documents related to at least one of the candidate subjects and one or more documents related to at least one of the known subjects;

generate a dictionary of a plurality terms each related to the known subjects or the candidate subjects and occur more than a threshold number of times in the collection of documents;

build a vector space model for the dictionary, wherein the vector space model has dimensions that correspond to frequencies of the plurality of terms included in the dictionary;

designate each document of the training set as a member of a first group of documents containing one or more of the known subjects or a member of a second group of documents containing one or more of the candidate subjects based on the vector space model;

determine feature vectors of the documents in the collection of documents, wherein the feature vectors include dimensions corresponding to frequencies of terms from the dictionary within the documents;

generate a classifier for the request from the dynamically generated training set using machine learning on the feature vectors of the designated documents of the training set in the first and second groups of documents;

apply the classifier to the feature vectors of the collection of documents to determine, for each candidate subject of the request, a quantity of documents for the candidate subject within the collection of documents classified as belonging to the first group of documents and a quantity of documents for the candidate subject within the collection of documents classified as belonging to the second group of documents;

generate a score for each candidate subject as a ratio of the quantity of documents for the candidate subject classified as belonging to the first group of documents to a total quantity of documents in the collection of documents for that candidate subject, wherein the score indicates a relationship of the candidate subject to the concept of interest and the total quantity of documents is a sum of the quantity of documents for the candidate subject within the collection of documents classified as belonging to the first group of documents and the quantity of documents for the candidate subject within the collection of documents classified as belonging to the second group of documents;

determine one or more of the candidate subjects of the request having a relationship to the concept of interest by ranking each of the candidate subjects of the request based on the determined score for each of the candidate subjects; and provide the ranked candidate subjects for display as a result of the request.

8. The computer program product of claim 7, wherein the classifier is applied to each document in the collection of documents.

9. The computer program product of claim 7, wherein at least one document of the training set is designated as a member of each of the first and second groups.

* * * * *